United States Patent [19]

Roman

[11] 4,281,183
[45] Jul. 28, 1981

[54] OXYIMINO-SUBSTITUTED CYCLOPROPANECARBOXYLATE

[75] Inventor: Steven A. Roman, Oakdale, Calif.

[73] Assignee: Shell Oil Company, Houston, Tex.

[21] Appl. No.: 156,894

[22] Filed: Jun. 5, 1980

Related U.S. Application Data

[62] Division of Ser. No. 51,668, Jun. 25, 1979, Pat. No. 4,237,123.

[51] Int. Cl.$^3$ .................... C07C 61/04; C07C 131/02
[52] U.S. Cl. .................................. 562/506; 542/416; 562/430; 562/432; 562/440; 562/500
[58] Field of Search ............... 562/440, 500, 506, 430, 562/432; 542/416

[56] References Cited

U.S. PATENT DOCUMENTS

| 3,922,269 | 11/1975 | Elliott et al. ....................... 260/347.4 |
| 4,219,563 | 8/1980 | Powell ................................... 562/506 |
| 4,219,565 | 8/1980 | Roman .................................. 562/506 |
| 4,223,155 | 9/1980 | Roman .................................. 562/506 |

OTHER PUBLICATIONS

Elliott et al., J. Chem. Soc., Perkin, I., (1974), pp. 2470-2474.

Primary Examiner—Arthur P. Demers

[57] ABSTRACT

New cyclopropane compounds have the formula

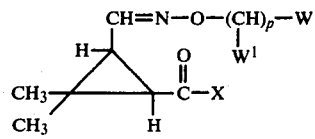

wherein
  X is chlorine, bromine or OR in which
  R is hydrogen, a salt-forming cation, an alkyl group or residues of certain other alcohols; and
  W is thienyl, furfuryl, —CO$_2$R$^1$, —CONR$^1$R$^2$, —SO$_3$R$^1$, —SO$_2$NR$^1$R$^2$, —PO$_3$H, —PO(OR$^1$)$_2$, —NO$_2$, —CN, —OR$^1$, —SR$^1$, —S(O)R$^1$, —S-(O)$_2$R$^1$, —NR$^1$R$^2$, —N(O)R$^1$R$^2$, or —(OCH$_2$CH$_2$-)$_q$—OR$^1$ in which R$^1$ and R$^2$ are H or certain optionally-substituted hydrocarbyl groups, q is 1–4, p is 1 or 2 and when p is 1 then W$^1$ is alkyl or when p is 2 then W$^1$ is H. The compounds are pesticides or intermediates therefore.

6 Claims, No Drawings

OXYIMINO-SUBSTITUTED CYCLOPROPANECARBOXYLATE

This is a division of application Ser. No. 51,668, filed June 25, 1979, now U.S. Pat. No. 4,237,123.

BACKGROUND OF THE INVENTION

1. Field of the Invention

This invention is directed to new oxyimino-substituted compounds, their use as pesticides, to pesticidal formulations containing these new compounds and to certain novel intermediates.

2. Description of the Prior Art

U.S. Pat. No. 3,922,269 describes a class of 2,2-dimethyl-3-(oxyiminomethyl)cyclopropanecarboxylic acid esters useful as insecticides.

SUMMARY OF THE INVENTION

It has now been found that certain oxyimino-substituted cyclopropanecarboxylates, especially those from the (1R,cis)-form of 2,2-dimethyl-3-formyl-cyclopropanecarboxylic acid, are useful pesticides (insecticides and acaricides) and exhibit high knockdown characteristics.

Therefore, this invention is directed to new cyclopropane compounds having the formula

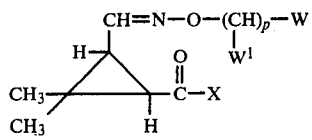

wherein W is thienyl, furfuryl, $-CO_2R^1$, $-CONR^1R^2$, $-SO_3R^1$, $-SO_2NR^1R^2$, $-PO(OR^1)_2$, $-NO_2$, $-CN$, $-OR^1$, $-SR^1$, $-S(O)R^1$, $-S(O)_2R^1$, $-NR^1R^2$, $-N(O)R^1R^2$ or $-(OCH_2CH_2)_q-OR^1$ in which q is an integer of 1 to 4, $R^1$ and $R^2$ each independently is a hydrogen atom, an alkyl group containing from 1 to 8 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms optionally substituted by one or more halogen atoms or an alkynyl group containing from 3 to 4 carbon atoms or an aryl group containing from 6 to 12 carbon atoms or an aralkyl group containing from 7 to 10 carbon atoms, each optionally ring-substituted by one or more halogen atoms or $R^1$ and $R^2$ taken together is an alkylene or oxaalkylene group containing from 4 to 6 carbon atoms, or when one of $R^1$ and $R^2$ is furfuryl or thienyl then the other is a hydrogen atom; p is an integer of 1 or 2; when p is 1 then $W^1$ is a hydrogen atom or an alkyl group containing from 1 to 4 carbon atoms or when p is 2 then $W^1$ is a hydrogen atom; X is chlorine, bromine or OR in which R represents a hydrogen atom, a salt-forming cation, an alkyl group containing from 1 to 20 carbon atoms or a group of the formula

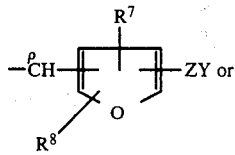

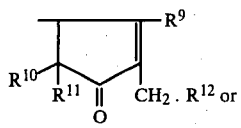

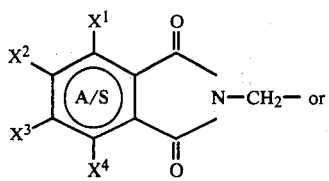

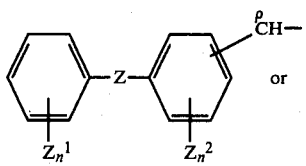

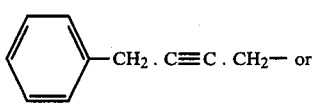

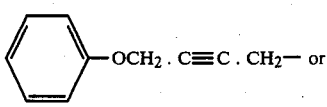

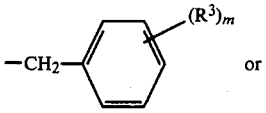

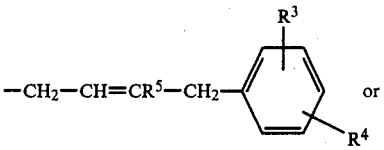

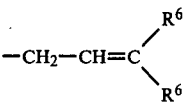

wherein Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represent hydrogen or an alkyl or alkenyl group, $R^9$ represents hydrogen or a methyl group, $R^{10}$ and $R^{11}$ represent hydrogen or an alkyl group, $R^{12}$ represents an organic radical having carbon-carbon unsaturation in a position α to the $CH_2$ group to which $R^{12}$ is attached, A/S indicates an aromatic ring or a dihydro or tetrahydro analogue thereof, $X^1$, $X^2$, $X^3$ and $X^4$, which may be the same or different, each represents hydrogen, halogen or a methyl group, D represents H, $-CN$,

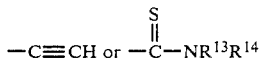

in which $R^{13}$ and $R^{14}$ may be the same or different, each represent a hydrogen atom or an alkyl group containing from 1 to 10 carbon atoms, Z represents —$CH_2$—, —O—, —CO— or —S—, $Z^1$ and $Z^2$, which may be the same or different, each represent halogen or an alkyl group containing 1 to 4 carbon atoms and n is 0, 1 or 2, $R^3$ and $R^4$ each independently is a hydrogen atom, a halogen atom having an atomic number of from 9 to 35, inclusive, an alkyl group containing from 1 to 4 carbon atoms or a nitro group, $R^5$ is a hydrogen atom or a halogen atom having an atomic number of from 9 to 35, inclusive, each $R^6$ is independently a halogen atom having an atomic number of from 9 to 35, inclusive; and m is an integer of from 1 to 5 with the proviso that when D is —CN,

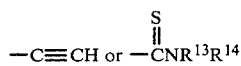

then the alcohol moiety is in the R,S-racemic or in the S-optical configuration.

In the above formulas, suitable halogen atom substituents are chlorine, fluorine or bromine.

The cyclopropane compounds exhibit optical isomerism by virtue of the two asymmetric centers in the cyclopropane ring. Consequently, the compounds can be prepared in optically active forms, which can subsequently be mixed together, or as racemic mixtures, which can subsequently be prepared as optically active forms. Because they usually provide the highest degree of pest control, the (1R, cis) esters are preferred although the (1R,trans) esters are also active. In the esters of α-substituted alcohols in which D in formulas I or IV is other than hydrogen, there is a further possibility of optical isomerism, i.e., as R or as S optical configuration. The cyano esters in which these alcohols exist in the R optical configuration are without practical pest control activity. In addition, optically active forms can be separated into the individual geometrical isomers.

The oxime substituent group of the compounds of the invention gives rise to geometric isomerism by virtue of the presence of an asymmetrically substituted double bond. These isomers are usually described as follows:

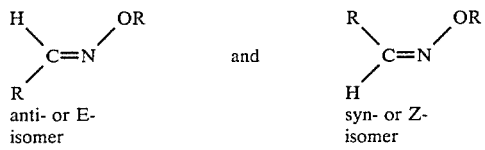

A useful subclass of the invention comprises esters in which the oxime substitutent is in the Z-isomer form as such isomers can be several times more pesticidally active than when the oxime substituent is in the E-isomer form or is a mixture of the E- and Z-isomer forms.

Since the biological activity of various optical or geometric isomers and diastereoisomer pairs in the esters of the invention wherein X is OR in which R is a group of formulas I–IX may differ somewhat, it may be desirable to use a more active optical and/or geometric isomer or diastereoisomer pair of the invention substantially free of the other isomers or pair.

The esters of the present invention wherein R represents a group of formula I–IX above are pesticidally active.

The oxyimino-substituted cyclopropane compounds described above in which X is chlorine, bromine or OR in which R represents a hydrogen atom, a salt-forming cation or an alkyl group are useful intermediates for the production of the pesticidal esters.

When the ester is one formally derivable from a furylmethyl alcohol, it is preferred that the furylmethyl alcohol be a 3-furylmethyl alcohol as described and claimed in U.S. Pat. No. 3,466,304.

In the furylmethyl alcohols (R is formula I), and particularly in the 3-furylmethyl alcohols, it is preferred that $R^7$ and $R^8$ each represents hydrogen or groups containing up to 4 carbon atoms, particularly a methyl group and that Y represents a phenyl group which is unsubstituted or substituted in the ring by a group containing up to 4 carbon atoms, e.g., methyl or methoxy, or by chlorine and Z is $CH_2$ and D is H. Analogues of these compounds where Z is O, S or CO and D is CN or C≡CH are also of interest. Further compounds of interest are those where Y represents a hydrogen atom, an alkyl group containing up to 4 carbon atoms, an alkenyl group containing up to 4 carbon atoms, e.g., vinyl, an alkadienyl group containing up to 4 carbon atoms or an alkynyl group, e.g., propargyl, or a furyl group.

Specific alcohols of this category, from which the esters of the invention are formally derivable, include 5-benzyl-3-furylmethyl alcohol, 5-benzyl-2-methyl-3-furylmethyl alcohol, 4-benzyl-5-methyl-2-furylmethyl alcohol, 5-(p-methylbenzyl)methyl-3-furylmethyl alcohol, 2,4,5-trimethyl-3-furylmethyl alcohol and 4,5-dimethyl-2-furylmethyl alcohol, 5-phenoxy- and 5-benzoyl-3-furylmethyl alcohol and α-cyano substituted 5-benzyl-, 5-benzoyl- or 5-phenoxy-3-furylmethyl alcohol.

The cyclopentenolones from which the esters of the invention are formally derivable are those unsubstituted in the 3-position or those substituted in the 3-position by a methyl group ($R^9$=H or $CH_3$).

The cyclopentenolones (R is formula II) unsubstituted in the 2-position are described and claimed in U.S. Pat. No. 3,720,703.

Some of these alcohols are the 3-desmethyl analogues of the alcohols from which the naturally occurring pyrethrins are derived. In the present invention, it is preferred that $R^{10}$ and $R^{11}$ each represents hydrogen, methyl or ethyl and $R^{12}$ represents an aryl group such as a phenyl group or a phenyl group substituted by a halogeno or alkyl or alkoxy substituent of 1 to 4 carbon atoms, for example tolyl, xylyl, p-chlorophenyl or p-methoxyphenyl. $R^{12}$ may also represent a 2- or 3-furyl group or an alkenyl group such as vinyl, 1-propenyl or 1,3-butadienyl group.

When the esters of the invention are formally derivable from the cyclopentenolones which are substituted in the 3-position by the methyl group ($R^9$=$R^{11}$=H, $R^{12}$=vinyl), pyrethrolone ($R^{10}$=$R^{11}$=H, $R^{12}$=1,3-butadienyl), cinerolone ($R^{10}$=$R^{11}$=H, $R^{12}$=1-propenyl), jasmolone ($R^{10}$=$R^{11}$=H, $R^{12}$=1-butenyl), or furethrolone ($R^{10}$=$R^{11}$=H, $R^{12}$=2-furyl).

When the esters of the invention are phthalimidomethyl esters where R is of formula III, they may be phthalimido, dihydrophthalimido or tetrahydrophthalimidomethyl esters where the phthalimido, dihydrophthalimido or tetrahydrophthalimido residue (R is formula III) is one described in British Pat. Nos. 985,006, 1,052,119 or 1,058,309. 3,4,5,6-Tetrahydrophthalimidomethyl esters are of particular interest.

When the esters of the invention are those where R is of formula IV, it is preferred that they be 3-benzylbenzyl esters, 3-benzoylbenzyl or 3-phenoxybenzyl esters although each of the rings may be substituted by up to 3 chloro and/or methyl groups. Other esters of particular interest where R is of formula IV are those where Z represents O or $CH_2$ and D represents CN or C≡CH, e.g., esters of α-cyano or α-ethynyl substituted 3-phenoxy-, 3-benzyl or 3-benzyloxybenzyl alcohol. Such alcohols are described in U.S. Pat. Nos. 3,666,789, 3,835,176 and 3,862,174.

The alcohols, from which the substituent R as a group of the formulas I–III is derived, are known in the art as, for example, in U.S. Pat. Nos. 3,567,740 and 3,683,005 and Hatch et al., *J. Amer. Chem. Soc.*, 79, pages 3091–3 (1957).

Suitable routes to the esters in which D is $$-\overset{S}{\underset{\|}{C}}NR^{13}R^{14}$$

are similar to those described in Belgian Pat. No. 839,360. One route involves treating the corresponding nitrile (D is —CN) with hydrogen sulfide in the presence of a basic catalyst, preferably in the presence of a solvent. Useful solvents are lower alkanols, pyridine, or preferably a dipolar aprotic solvent, such as dimethylformamide or hexamethylphosphoramide. The catalyst is preferably a strong nitrogeneous base, particularly a tertiary amine such as triethylamine, trimethylamine, or the like, or an alkanolamine, such as triethanolamine and the like. The reaction can be carried out at room temperature. It is desirable that the reaction solution be saturated with hydrogen sulfide.

Examples of species within the scope of the present invention include:
α-cyano-3-phenoxybenzyl 2,2-dimethyl-3-((2-(dimethylamino)-2-oxoethoxyimino)methyl)cyclopropanecarboxylate,
pentachlorobenzyl 2,2-dimethyl-3-((2-(dimethylsulfamoyl)ethoxyimino)methyl)cyclopropanecarboxylate,
5-benzyl-3-furylmethyl 2,2-dimethyl-3-((2-(dimethoxyphosphinyl)ethoxyimino)methyl)cyclopropanecarboxylate,
3-chloro-4-phenyl-2-buten-1-yl 2,2-dimethyl-3-((2-(nitroethoxy)imino)methyl)cyclopropanecarboxylate,
3,3-dichloropropen-2-yl 2,2-dimethyl-3-((2-(cyano)ethoxyimino)methyl)cyclopropanecarboxylate,
3-phenoxybenzyl 2,2-dimethyl-3-((2-(dimethylamino)ethoxyimino)methyl)cyclopropanecarboxylate,
α-ethynyl-3-phenoxybenzyl 2,2-dimethyl-3-(((2-methoxy)ethoxyimino)methyl)cyclopropanecarboxylate,
α-thiocarbamoyl-3-phenoxybenzyl 2,2-dimethyl-3-((2-(methylthio)ethoxyimino)methyl)cyclopropanecarboxylate,
3-phenylthiobenzyl 2,2-dimethyl-3-(((methylsulfonyl)methoxyimino)methyl)cyclopropanecarboxylate, Preferably, W is thienyl, furfuryl, —$CO_2R^1$, —$OR^1$ or —$SR^1$ in which $R^1$ is a hydrogen atom, an alkyl group containing from 1 to 5 carbon atoms or a cycloalkyl group containing 3 or 4 carbon atoms; p is 1 or 2; and $W^1$ is a hydrogen atom. Suitably, $R^1$ is a methyl group.

Because of their pesticidal utility in agricultural and domestic situations, preferred compounds of the invention (subject to the same provisions stated above) are those wherein R is 5-benzyl-3-furylmethyl, α-cyano-3-phenoxybenzyl, 3-phenoxybenzyl or α-ethynyl-3-phenoxybenzyl, 2,6-dichlorobenzyl or pentachlorobenzyl. A particularly preferred subclass of the invention are those esters derived from the S-α-cyano-3-phenoxybenzyl alcohol. Especially when the acid moiety of such esters is in the (1R,cis) form.

The alkyl esters of the present invention can also be prepared by treating an ester of caronaldehydic acid of formula XIII

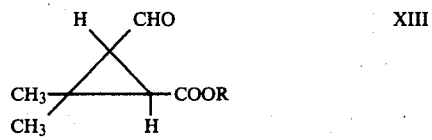

where R is an alkyl group, with hydroxylamine or an O-substituted hydroxylamine of formula $R^1ONH_2$ where $R^1$ is as defined above, and in the case where $R^1$ represents hydrogen, subsequently hydrocarbylating the resulting oxime, if desired, with the desired hydrocarbyl halide or the like, to give a hydrocarbyloxime. Oxime formation can take place by treating substantially equimolar amounts of aldehyde and hydroxylamine or hydrocarbyloxyamine in a polar solvent such as an alkanol, e.g., ethanol or dioxane. When the aldehyde is converted into the oxime by reaction with hydroxylamine and it is desired to convert the resulting oxime into the hydrocarbylated (alkylated) derivatives or the like, this reaction may be carried out by procedures customarily used for the alkylation of phenols. Thus, the oxime may be treated in a polar solvent, such as ethanol, with an alkyl halide, typically the bromide, in the presence of a hydrogen halide acceptor and the mixture heated until reaction is complete. Oxime formation is normally carried out using an acid addition salt of hydroxylamine or the hydrocarbyloxyamine, e.g., the hydrochloride.

Alcohols and halides of formula XI are described and claimed in U.S. Pat. No. 3,720,703.

Alcohols of formula RQ where R is a group of formula IV may be prepared by reduction of the corresponding acids or esters or aldehyde, e.g., with hydride, or by conversion of the corresponding halide to an ester, e.g., by reaction with sodium acetate, followed by hydrolysis of the ester, or by reaction of formaldehyde with a Grignard reagent derived from the corresponding halide. The halides of formula RQ where R is a group of formula IV can be prepared by halomethylation of the compound

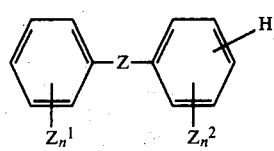

or side chain halogenation of

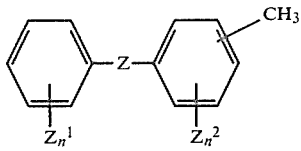

When R is a salt-forming cation, it is selected from alkali metals, alkaline earth metals, aluminum, heavy metals, such as copper, silver, nickel and the like, ammonia or a tetrahydrocarbylammonium compound in which the total number of carbon atoms in the hydrocarbyl groups is between 4 and 70 carbon atoms. The hydrocarbyl groups can be alkyl, aryl, aralkyl and the like. Preferably, the hydrocarbyl groups are selected from alkyl groups containing from 1 to 10 carbon atoms and aralkyl groups containing from 7 to 10 carbon atoms.

When R is an alkyl group, it contains from 1 to 20 carbon atoms, and preferably from 1 to 6 carbon atoms, for example, methyl, ethyl, n-propyl, tert-butyl and the like.

The pesticidal esters of the present invention may be prepared by esterification involving the reaction of an alcohol or derivative thereof of formula RQ e.g., of formula XIV or XV, and a cyclopropane carboxylic acid or derivative thereof of formula XVI

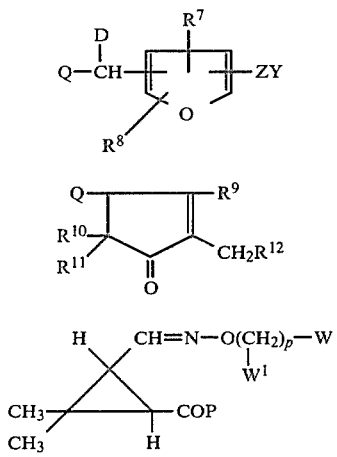

where Q and COP are functional groups or atoms which will react to form an ester linkage and $R^7$, $R^8$, $R^9$, $R^{10}$, $R^{11}$, $R^{12}$, D, p, W, $W^1$ and Y are as defined above.

It is usually convenient in practice either to treat the acid or acid halide with the alcohol (COP=COOH or CO-halide and Q=OH) or to treat a halogeno compound (Q=halogen) with a salt of the carboxylic acid (COP=COO—M where M is, for example, a silver or triethylammonium cation).

Transesterification is not always practical and, it is useful to prepare the intermediate alkyl ester as a tert-butyl ester (R=tertbutyl) which can be selectively converted (under acid conditions) to give the free acid which can, after conversion to the acid halide, be esterified to a pesticidal ester.

The O-substituted hydroxylamine salt intermediates used to prepare the cyclopropane carboxylic acids of the invention wherein X is —OH are prepared by esterifying N-hydroxyphthalimide using a hydrocarbyl halide or other esterifying reactant to introduce the desired function —(CH2)$_p$—W and converting the resulting ester into the corresponding O-substituted hydroxylamine salt,

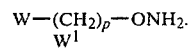

A wherein W, $W^1$ and p are defined above and A is the anion of a salt-forming acid. Suitable inorganic acids include hydrohalogenic acids such as hydrochloric and hydrobromic acids, sulfur acids such as sulfuric and fluorosulfonic acids, phosphorus acids such as phosphoric acid, nitrogen acids such as nitric acid or boron acids such as boric and fluoroboric acids. Organic acids, such as oxalic, malonic and succinic acids are also suitable. This conversion is conducted by first treating the N-alkoxyphthalimide with an acid, such as a mixture of concentrated hydrochloric acid with glacial acetic acid (or with other suitable reagents known in the art, such as with hydrazine in ethanol), neutralizing the resulting reaction mixture and then adding the salt-forming acid. Alternatively, an alkali metal alkoxide can be treated with chloramine and the resulting reaction product treated with the salt-forming acid.

The O-substituted hydroxylamine salt is then reacted with caronaldehydic acid, which has previously been described, for example, in U.S. Pat. Nos. 3,723,469 and 3,922,269 to yield the desired cyclopropanecarboxylic acid. The reaction is preferably conducted in an aqueous medium in the presence of a buffer, such as an alkali metal salt of a polybasic acid, including sodium hydrogen carbonate, potassium hydrogen tartrate, disodium hydrogen phosphate and the like. Generally, at least one mole of buffer is used for each mole of caronaldehydic acid. The molar ratio of reactants is not critical and can be widely varied, generally a molar ratio of the O-substituted hydroxylamine salt to caronaldehydic acid is suitably from about 1.0 to about 1.5 and preferably from about 1.02 to about 1.3. The reaction is generally conducted in the liquid phase by agitating, e.g., stirring, a mixture of the reactants. The resulting product is recovered by conventional techniques such as filtering, extracting or the like. The reaction temperature is not critical and can easily range from ambient to the reflux temperature of any solvent employed at normal pressure. Generally, the temperature is between about 0° C. to about 50° C. A minor amount of co-solvent can be used in the reaction medium. Suitable cosolvents are lower alcohols containing from 1 to 6 carbon atoms, such as methanol, ethanol and the like.

The resulting acids are converted to the ester compounds of the invention, for example, by reaction with the appropriate hydrocarbyl halide corresponding to the substituent of formulas I-IX, in the presence of triethylamine, in a solvent, such as refluxing ethyl acetate.

An isomer mixture of the esters of the invention is separated into the diastereoisomers using known procedures, as for example, by preparative scale liquid chromatography. One such chromatographic system which can be employed has the following characteristics:

Column—porisil polar bonded phase, 9.2×250 mm
Mobile Phase—8% v/v diethyl ether in n-hexane
Flow Rate—2.5 ml/min
Detection—UV$_{254}$ at 2.0 AUFS
Injection—typically 500 ml of a 20 mg/ml solution in the mobile phase.

Such a procedure readily yields the single diastereoisomers or diastereoisomer pairs, depending on the composition of the isomer mixture to be separated, in greater than 90% purity (as determined by NMR analysis). In the case of (1R,cis) esters of α-substituted alcohols four diastereoisomers are obtained.

Since it is believed that the esters of the invention in which the oxime substituent is in the Z-isomer form are pesticidally more active than when the oxime substituent is in either the E-isomer form or is a mixture of E- and Z-isomer forms, it can be desirable to convert the esters in E-isomer form into a mixture of esters in both the E- and Z-isomer forms. Such conversion is accomplished by the addition of a minor amount of an organic or inorganic acidic material. Any inorganic or organic acid or acidic acting material can be used, including acidic clays such as acidic silicates and aluminates or synthetic acidified clays, mineral acids such as hydrochloric or sulfuric acid, sulfonic acids such as toluenesulfonic acid, or organic acids, including lower alkanoic acids such as acetic, propionic or butyric acids. The acid can be used in a solid or liquid form. While the precise amount of acid used to convert the E-isomer or Z-isomer into the E- and Z-isomer mixture can vary depending on the particular oxyimino-substituted ester, from 0.001 to 5% by weight of acid based on the E-isomer or Z-isomer is generally sufficient. Preferably, from 0.01 to 5% by weight of acid is used.

As stated earlier, the esters wherein X is OR in which R is a group of formula I-IX are useful pest control agents having the ability to knock down insects, such as houseflies, or repel mites and/or to kill insects or mites. The particular mode of pest control activity (high knockdown, repelling or killing action) can vary with the individual cyclopropanecarboxylate ester of the invention and thus depends on the specific combination of acid and alcohol moieties.

The invention includes, within its scope, pesticidal compositions comprising a pesticidally acceptable adjuvant—that is, at least one carrier or a surface-active agent—and, as active ingredient, at least one pesticidally active ester of this invention. Likewise, the invention includes also a method of combatting insect, acarine or other arthropod pests at a locus which comprises applying to the pests or to the locus a pesticidally effective amount of at least one compound of the invention.

With respect to the spectrum of pesticidal activity, the compounds of this invention exhibit a selective or non-selective activity on such orders as Coleoptera, Lepidoptera (especially larvae), Diptera, Orthoptera, Hemiptera, Homoptera and Acarina depending upon a specific combination of acid and an alcohol according to the present invention. The compositions according to the present invention are very useful for controlling disease-carrying insects such as mosquitoes, flies and cockroaches, grain insects such as rice weevil (*Sitophilus oryzae*) and mites as well as agricultural noxious insects such as planthoppers, green rice leafhopper (*Nephotettix bipuntatus cinticeps* Uhler), diamondback moths (*Plutella maculipennis* Curtis), imported cabbage worm (*Pieris rapae* Linne), rice stem borers (*Chilo suppressalis* Walker), corn earworm larvae (*Heliothis zea* Boddie), aphids, tortrixes, leaf-miners and the like.

The esters are used for harvested crops, horticultural application, forests, cultures in green house, packaging materials for foodstuffs, household applications and as ectoparasiticides.

The term "carrier" as used herein means a material, that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified normally vaporous gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acids salts of low molecular weight, mono-, di- and trialkyl-amines; condensates of these with ethylene oxide and/or proplyene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by extrusion of plastics, agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, cosolvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for use with the general class of "pyrethroid" compounds, especially α-[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethyhexyl)bicyclo[2,2,1]hept-5-ene-2,3-dicarboximiide, octachlorodipropyl ether, isobornyl thiocyanoacetate, and other synergists used for allethrin and pyrethrin. Useful compositions can be prepared with other biological chemicals including other cyclopropanecarboxylates, organic phosphate type insecticides and carbamate type insecticides.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of the order or 0.01% to 0.5% based on the total weight of the formulation, though under some circumstances the effective concentration will be as little as 0.001% or as much as 2%, on the same basis.

The superior activity of the (1R,cis) esters of the invention is usefully employed when such an ester is present in an amount substantially greater than that usually present in the racemate of an oxyimino substituted ester. Therefore, use of the (1R,cis) esters of the invention in a form substantially free of other stereoisomers is preferred, for example in a (1R,cis) isomer purity of greater than about 85%, preferably in a (1R,cis) isomer purity greater than about 90% or even greater than 95%.

ILLUSTRATIVE EMBODIMENTS

The invention is illustrated by the following embodiments which describe the preparation and biological testing of typical species of the invention with respect to representative insects and acarines. The embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

EMBODIMENT I (1R,cis)-2,2-dimethyl-3-(((2-methoxyethoxy)imino)methyl)-cyclopropanecarboxylic acid To a solution of 38 g of 2-methoxyethanol in 12 ml of pyridine was added portionwise, over two hours, 95.3 g of p-toluenesulfonyl chloride at 0° C. The reaction mixture was stirred for 20 hours, poured into 200 ml of concentrated hydrochloric acid and 1 liter of ice cubes, extracted with methylene chloride and washed successively with methylene chloride, water and a saturated sodium chloride solution. The organic phase was dried over magnesium sulfate and stripped to yield 99 g of 2-methoxyethyl tosylate as a yellow oil.

The above tosylate was added to a stirred solution of 65.2 of N-hydroxyphthalimide and 33.2 g of sodium carbonate in 500 ml of dimethylformamide. The reaction mixture was heated on a steam bath, stirred for 4½ hours and poured into ice water. The solid product was filtered, washed with water, dissolved in methylene chloride and washed with water. The methylene chloride phase was dried over magnesium sulfate and stripped to give a solid which was recrystallized using a mixture of ethanol and hexane to yield 60 g of solid 2-(2-methoxyethoxy)-1H-isoindole-1,3(2H)-dione; m.p. 93.5°–94.5° C.

A 22.1 g portion of the isoindole product in 380 ml of a mixture of concentrated hydrochloric and glacial acetic acid (1–3.3 ratio) was mildly refluxed in an oil bath for 30 minutes. The reaction mixture was cooled, 30% sodium hydroxide solution was added to adjust the pH to between 9–10, and the mixture was extracted with ether. The ether extract was dried with calcium chloride and treated with a saturated solution of oxalic acid in ether to form a precipitate. The solids were filtered to give 3.2 g of 2-methoxyethoxyamine oxalate; m.p. 81°–3° C.

A 2.0 g portion of the above product, 1.4 g of (1R,cis)caronaldehydic acid and 2.8 g of sodium bicarbonate in 50 ml of water was stirred at room temperature for 4 hours. The reaction mixture was filtered through celite, and the filtrate was acidified and extracted with methylene chloride. The extract was washed with saturated sodium chloride solution, dried over magnesium sulfate, and stripped to yield 2.0 g of the desired acid product as an oil; $[\alpha]_D^{25} +22.5°$ (CHCl$_3$); c=0.02 g/cc.

EMBODIMENT II

α-Cyano-3-phenoxybenzyl (1R,cis)-1,2-dimethyl-3-(((2-methoxyethoxy)imino)methyl)cyclopropanecarboxylate To a solution of 0.55 g potassium carbonate, 0.05 g tetrabutylammonium sulfate, 0.05 g benzyltriethylammonium chloride in 6 ml water, was added 1.80 g of the acid, prepared in Embodiment I above, in 10 ml of toluene. The mixture was stirred rapidly with the addition of 2.10 g of α-cyano-3-phenoxybenzyl bromide and stirring was continued for 7 hours at 65°-70° C. The toluene phase was separated, washed successively with water, sodium bicarbonate solution and sodium chloride solution, dried over magnesium sulfate, and stripped to yield an oil. This oil was passed through a silica-gel column using ether/pentane (1:4) as the eluent to yield 2.7 g of a clear yellow oil product; $[\alpha]_D^{25} +12.5°$ (CHCl$_3$); c=0.02 g/cc.

EMBODIMENT III (1R,cis)-2,2-dimethyl-3-(((2-tert-butoxy)-2-oxoethoxyimino)methyl)cyclopropanecarboxylic acid To a solution of 49 g of N-hydroxyphthalimide in 25 ml of dimethyl sulfoxide at 5° C., was added portionwise 27.6 g of potassium carbonate. After 10 minutes of stirring the reaction mixture was present as a red slurry to which 75 g of tert-butyl chloroacetate was added dropwise over 1 hour at 5° C. The resulting reaction mixture was stirred for 18 hours and poured into ice water. The solid product was filtered, dissolved in methylene chloride and washed with water. The methylene chloride phase was dried over magnesium sulfate, filtered and stripped and recrystallized from ethanol to give 77.5 g of 2-(2-tertbutoxy-2-oxoethoxy)-1H-isoindole-1,3(2H)-dione; m.p. 146°-7° C.

A 27.7 g portion of the above isoindole product, 200 ml of ethanol and 11.8 g of hydrazide hydrate was refluxed on a steam bath for 1 hour. The resulting solid was dissolved by adding 500 ml of a 5% aqueous sodium carbonate solution, the solution was extracted with ether, dried with magnesium sulfate and added to a solution of 9 g of oxalic acid in 125 ml of ether to form a precipitate. The solids were filtered to give 13.9 g of 2-tert-butoxy-2-oxoethoxyamine oxalate; m.p. 125°-6° C.

A 2.6 g portion of the above product, 1.4 g of (1R,cis)caronaldehydic acid and 2.8 g of sodium bicarbonate in 50 ml of water was stirred for 16 hours at room temperature. The reaction mixture was filtered through celite, and the filtrate was acidified to pH 4 and extracted with methylene chloride. The extract was washed with saturated sodium chloride solution, dried over magnesium sulfate, filtered and stripped to yield 1.7 g of the desired acid product as an oil.

EMBODIMENTS IV-X

Using procedures similar to those employed in Embodiments I through III, the additional oxyiminocyclopropane derivatives were prepared as described in Table I below:

TABLE I

OXYIMINO-SUBSTITUTED (1R,CIS)-CYCLOPROPAECARBOXYLATES $$\text{structure with } CH=N-O-(CH)-W, \; CH_3, CH_3, H, \text{ and } C(=O)-O-R$$

| Embodiment | W | R | $[\alpha]_D^{25}$ (CHCl$_3$) |
|---|---|---|---|
| IV | —CO$_2$C(CH$_3$)$_3$ | α-cyano-3-phenoxybenzyl | +10.0° |
| V | furyl (O) | H | +32.5° |
| VI | furyl (O) | α-cyano-3-phenoxybenzyl | +10.0° |
| VII | thienyl (S) | H | +32.5° |
| VIII | thienyl (S) | α-cyano-3-phenoxybenzyl | +13.8° |
| IX | —SCH$_3$ | H | +37.5° |
| X | —SCH$_3$ | α-cyano-3-phenoxybenzyl | +20.0° |

EMBODIMENT XI

Pesticidal Activity

Activity of the compounds of this invention with respect to insect and acarine pests was determined by using standardized test methods to test the toxiciity of the compounds as follows:

I. Houseflies (*Musca domestica* (Linne)) were tested by placing 50 4- to 5-day old houseflies into a spray cage and spraying with 0.6 ml of a solution of test compound. After spraying, the flies were anesthetized with CO$_2$ and transferred to a recovery cage containing a milk pad for food. The cages were held for 18-20 hours after which mortality counts were made. Both dead and moribund were counted. The tests were conducted employing several different dosage rates of each test compound.

II. Pea aphids (*Acyrthosiphon pisum* (Harris)) were tested by placing about 100 aphids on broad bean plants. The plants were sprayed with dilutions of acetone solution of test compound into water containing an emulsifier and held in containers under laboratory conditions for 18 to 20 hours at which time the living aphids in the containers were counted. The tests were conducted employing several different dosage rates of each test compound.

III. Adult female two-spotted spider mites (*Tetranychus urticae* (Koch)) were tested by placing 50-75 mites on the bottom side of leaves of pinto bean plants. The leaves were sprayed with dilutions of acetone solution of test compound into water containing an emulsifier and kept under laboratory conditions for about 20 hours at which time mortality counts were made. The test were conducted employing several different dosage rates of test compounds.

IV. Mosquito larvae (*Anopheles albimanus* (Weide)) were tested by placing ten living and active mosquito larvae in a jar containing a 0.1 ml aliquot of a 1% acetone solution of test compound thoroughly mixed with 100 ml of distilled water. After 18-22 hours, mortality counts were taken. Both dead and moribund larvae were counted as dead. Larvae which did not swim after being prodded with a needle were considered moribund. The tests were conducted employing several different dosage rate for each test compound.

V. Corn earworm larvae (*Heliothis zea* (Boddie)) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insects or acarine. Assigning the standard pesticide an arbitrary rating of 100, the toxicities of the compounds of the invention were expressed in terms of the toxicity indexes, which compares the toxicity of the compounds of the invention with that of the standard pesticide. That is to say, a test compound having a Toxicity Index of 50 would be half as active, whereas one having a Toxicity Index of 200 would be twice as active as the standard pesticide.

Results of the above tests are shown in Table II.

TABLE II.

PESTICIDAL ACTIVITY OF CYCLOPROPANECARBOXYLATE OXIMES EXPRESSED AS TOXICITY INDEX RELATIVE TO THAT OF PARATHION AS A STANDARD EQUAL TO 100

| Embodiment | House-fly | Pea Aphid | 2-Spotted Mite | Mosquito Larvae | Corn Earworm |
|---|---|---|---|---|---|
| II | 39 | 110 | 4 | 4 | 120 |
| IV | 20 | 520 | 5 | 19 | 140 |
| VI | 62 | 48 | 0 | 3 | 65 |
| VIII | 48 | 76 | 27 | + | 180 |
| X | 69 | 70 | 16 | 11 | 170 |

+ means "low toxicity".

I claim:

1. A cyclopropane compound having the formula

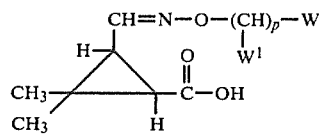

wherein W is $-OR^1$, $-SR^1$, $-S(O)R^1$, $-S(O)_2R^1$, $-NR^1R^2$, $-N(O)R^1R^2$ or $-(OCH_2CH_2)_q-OR^1$ in which q is an integer of 1 to 4, $R^1$ and $R^2$ each independently is a hydrogen atom, an alkyl group containing from 1 to 8 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms optionally substituted by one or more halogen atoms or an alkynyl group containing from 3 to 4 carbon atoms or an aryl group containing from 6 to 12 carbon atoms or an aralkyl group containing from 7 to 10 carbon atoms, each optionally ring-substituted by one or more halogen atoms or when p is 2 then $W^1$ is a hydrogen atom.

2. A cyclopropane compound according to claim 1 wherein W is $-OR^1$ or $-SR^1$ in which $R^1$ is a hydrogen atom, an alkyl group containing from 1 to 5 carbon atoms or a cycloalkyl group containing 3 or 4 carbon atoms; p is 1 or 2; and $W^1$ is a hydrogen atom.

3. A cyclopropane compound according to claim 2 wherein W is $-OR^1$ or $-SR^1$ in which $R^1$ is a hydrogen atom or an alkyl group containing from 1 to 5 carbon atoms.

4. A cyclopropane compound according to claim 3 wherein W is $-OCH_3$.

5. A cyclopropane compound according to claim 3 wherein W is $-SCH_3$.

6. A cyclopropane compound according to claim 1 wherein W is $-OCH_3$, p is 2 and $W^1$ is H.

* * * * *